US006615082B1

(12) United States Patent
Mandell

(10) Patent No.: US 6,615,082 B1
(45) Date of Patent: Sep. 2, 2003

(54) METHOD AND DEVICE FOR OPTIMALLY ALTERING STIMULATION ENERGY TO MAINTAIN CAPTURE OF CARDIAC TISSUE

(75) Inventor: Lee J. Mandell, West Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 257 days.

(21) Appl. No.: 09/685,331

(22) Filed: Oct. 5, 2000

Related U.S. Application Data

(60) Provisional application No. 60/204,317, filed on May 15, 2000.

(51) Int. Cl.[7] ................................................ A61N 1/26
(52) U.S. Cl. .............................. 607/11; 607/5; 607/9; 607/17; 607/28
(58) Field of Search ............................ 607/9, 11, 17, 607/12, 28, 5

(56) References Cited

U.S. PATENT DOCUMENTS

| | | | |
|---|---|---|---|
| 4,590,941 A | 5/1986 | Saulson et al. | 128/419 PG |
| 4,712,555 A | 12/1987 | Thornander et al. | 128/419 PG |
| 4,788,980 A | 12/1988 | Mann et al. | 128/419 PG |
| 4,809,697 A | 3/1989 | Causey, III et al. | 128/419 PT |
| 4,940,052 A | 7/1990 | Mann et al. | 128/419 PG |
| 4,944,298 A | 7/1990 | Sholder | 128/419 PG |
| 4,944,299 A | 7/1990 | Silvian | 128/419 PG |
| 4,979,507 A | 12/1990 | Heinz et al. | 128/419 PG |
| 5,320,643 A | 6/1994 | Roline et al. | 607/28 |
| 5,441,521 A * | 8/1995 | Hedberg | 607/6 |
| 5,447,525 A | 9/1995 | Powell et al. | 607/28 |
| 5,476,487 A * | 12/1995 | Sholder | 607/28 |
| 5,653,735 A * | 8/1997 | Chen et al. | 607/9 |
| 5,697,956 A | 12/1997 | Bornzin | 607/28 |
| 5,718,720 A | 2/1998 | Prutchi et al. | 607/28 |
| 6,430,441 B1 * | 8/2002 | Levine | 607/28 |

OTHER PUBLICATIONS

Danilovic, Dejan et al., Pacing Threshold Trends and Variability in Modern Tined Leads Assessed Using High Resolution Automatic Measurements: Conversion of Pulse width into Voltage Thresholds, PACE, vol. 22, (Part 1), pp 567–587 (Apr. 1999).

Coates, Stephen et al., The Strength–Duration Curve and Its Importance in Pacing Efficiency: A Study of 325 Pacing Leads in 229 Patients, PACE, vol. 23, pp 1273–1277 (Aug. 2000).

Raschack, M., Differences in the Cardiac Actions of the Calcium Antagonists Verapamil and Nifedipine, Arzneim–Forsch. (Drug. Res.) 26, Nr. 7 (1976), pp 1330–1333.

Pacesetter®, "Affinity™ DR Model 5330 L/R, Dual–Chamber Pulse Generator with Autocapture® Pacing System", 1998 St. Jude Medical, Inc., pp. 1–76.

Peck, Bradley, Current Concepts in Autocapture, Medtronic® Technical Concept Paper, pp 1–4 (Dec. 1998).

* cited by examiner

Primary Examiner—Hieu T. Vo
Assistant Examiner—Johnny H. Hoang

(57) ABSTRACT

An improved system and method for performing automatic capture/threshold detection in an implantable cardiac stimulation device or any device capable of stimulating some organ or tissue in the body. Prior art systems determine the stimulation threshold of the cardiac tissue by detecting an evoked response to a fixed duration stimulation pulse and then increasing the amplitude of the stimulation pulse by a predetermined safety margin value. Such systems are inherently based upon a belief that the chronaxie of the strength-duration curve for a particular patient is essentially fixed and that the rheobase is variable. While this may be true at some times during the patient's life, e.g., during the acute phase after lead implantation absent drug effects, it is reported that drugs alone may alter the chronaxie and it is believed that other factors may also affect the chronaxie either alone or in combination with the rheobase.

54 Claims, 10 Drawing Sheets

|  | AMPLITUDE | DURATION | |
|---|---|---|---|
| 0 | .40 | .00 | 900 |
| 1 | .45 | .05 | |
| 2 | .50 | .10 | |
| 3 | .55 | .15 | |
| 4 | .60 | .20 | |
| 5 | .65 | .25 | |
| 6 | .70 | .30 | ← ORIGINAL CHRONAXIE POINT |
| 7 | .75 | .35 | |
| 8 | .80 | .40 | ← + SAFETY MARGIN |
| 9 | .85 | .45 | |
| 10 | .90 | .50 | |
| 11 | .95 | .55 | |
| 12 | 1.00 | .60 | |
| 13 | 1.05 | .65 | |
| 14 | 1.10 | .70 | |
| 15 | 1.15 | .75 | |
| 16 | 1.20 | .80 | |
| 17 | 1.25 | .85 | ← CAPTURE |
| 18 | 1.30 | .90 | |
| 19 | 1.35 | .95 | ← + SAFETY MARGIN |
| 20 | 1.40 | 1.00 | |
| ⋮ | | | |
| N | | | |

FIG. 10

|  | AMPLITUDE | DURATION |
|---|---|---|
| 0 | .35 | .00 |
| 1 | .40 | .05 |
| 2 | .45 | .10 |
| 3 | .50 | .15 |
| 4 | .55 | .20 |
| 5 | .60 | .25 |
| 6 | .65 | .30 | ← QUASI-CHRONAXIE
| 7 | .70 | .35 |
| 8 | .75 | .40 | ← + SAFETY MARGIN
| 9 | .80 | .45 |
| 10 | .85 | .50 |
| 11 | .90 | .55 |
| 12 | .95 | .60 |
| 13 | 1.00 | .65 |
| 14 | 1.05 | .70 |
| 15 | 1.10 | .75 |
| 16 | 1.15 | .80 |
| 17 | 1.20 | .85 | ← CAPTURE
| 18 | 1.25 | .90 |
| 19 | 1.30 | .95 | ← + SAFETY MARGIN
| 20 | 1.35 | 1.00 |
| ⋮ N | | |

METHOD AND DEVICE FOR OPTIMALLY ALTERING STIMULATION ENERGY TO MAINTAIN CAPTURE OF CARDIAC TISSUE

This application claims the benefit of U.S. Provisional Application No. 60/204,317, filed May 15, 2000.

FIELD OF THE INVENTION

The present invention is generally directed to an implantable medical device, e.g., a cardiac stimulation device, and is particularly directed to an automatic capture/threshold pacing method for use in such a device.

BACKGROUND OF THE INVENTION

Implantable cardiac stimulation devices are well known in the art. They include implantable pacemakers which provide stimulation pulses to cause a heart, which would normally beat too slowly or at an irregular rate, to beat at a controlled normal rate. They also include defibrillators which detect when the atria and/or the ventricles of the heart are in fibrillation or a pathologic rapid organized rhythm and apply cardioverting or defibrillating electrical energy to the heart to restore the heart to a normal rhythm. Implantable cardiac stimulation devices may also include the combined functions of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation pulses when they are needed and inhibit the delivery of cardiac stimulation pulses at other times. This inhibition accomplishes two primary functions. Firstly, when the heart is intrinsically stimulated, its hemodynamics are generally improved. Secondly, inhibiting the delivery of a cardiac stimulation pulse reduces the battery current drain on that cycle and extends the life of the battery which powers and is located within the implantable cardiac stimulation device. Extending the battery life will therefore delay the need to explant and replace the cardiac stimulation device due to an expended battery. Generally, the circuitry used in implantable cardiac stimulation devices have been significantly improved since their introduction such that the major limitation of the battery life is primarily the number and amplitude of the pulses being delivered to a patient's heart. Accordingly, it is preferable to minimize the number of pulses delivered by using this inhibition function and to minimize the amplitude of the pulses where this is clinically appropriate.

It is well known that the amplitude of a pulse that will reliably stimulate a patient's heart, i.e., its threshold value, will change over time after implantation and will vary with the patient's activity level and other physiological factors. To accommodate for these changes, pacemakers may be programmed manually by a medical practitioner to deliver a pulse at an amplitude well above an observed threshold value. To avoid wasting battery energy, the capability was developed to automatically adjust the pulse amplitude to accommodate for these long and short term physiological changes. In an existing device, the Affinity® DR, Model 5330 L/R Dual-Chamber Pulse Generator, manufactured by the assignee of the present invention, an AutoCapture™ pacing system is provided. The User's Manual, ©1998 St. Jude Medical, which describes this capability is incorporated herein by reference. In this system, the threshold amplitude level is automatically determined for a predetermined duration level in a threshold search routine and capture is maintained by a capture verification routine. Once the threshold search routine has determined a pulse amplitude that will reliably stimulate, i.e., capture, the patient's heart, the capture verification routine monitors signals from the patient's heart to identify pulses that do not stimulate the patient's heart (indicating a loss-of-capture). Should a loss-of-capture (LOC) occur, the capture verification routine will generate a large amplitude (e.g., 4.5 volt) backup pulse shortly after (typically within 80–100 milliseconds) the original (primary) stimulation pulse. This capture verification occurs on a pulse-by-pulse basis and thus, the patient's heart will not miss a beat. However, while capture verification ensures the patient's safety, the delivery of two stimulation pulses (with the second stimulation pulse typically being much larger in amplitude) is potentially wasteful of a limited resource, the battery capacity. To avoid this condition, the existing device, monitors for two consecutive loss-of-capture events and only increases the amplitude of the primary stimulation pulse should two consecutive loss-of-capture (LOC) events occur, i.e., according to a loss-of-capture criteria. This procedure is repeated, if necessary, until two consecutive pulses are captured, at which time a threshold search routine will occur. The threshold search routine decreases the primary pulse amplitude until capture is lost on two consecutive pulses and then, in a similar manner to that previously described, increases the pulse amplitude until two consecutive captures are detected. This is defined as the capture threshold. The primary pulse amplitude is then increased by a safety margin value, e.g., 0.3 volts, to ensure a primary pulse whose amplitude will exceed the threshold value and thus reliably capture the patient's heart without the need for frequent backup pulses. In a copending, commonly-assigned U.S. patent application Ser. No. 09/483,908 to Paul A. Levine, entitled "An Implantable Cardiac Stimulation Device Having Autocapture/Autothreshold Capability", improved loss-of-capture criteria are disclosed which are based upon X out of the last Y beats, where Y is greater than 2 and X is less than Y. The Levine application is incorporated herein by reference in its entirety.

Whether a stimulation pulse successfully captures muscle, e.g., cardiac, tissue and thus causes the muscle to contract is related to an amplitude component, i.e., voltage or current, and a duration component of the stimulation pulse. This relationship was described in 1909 by Lapicque as a strength-duration curve (see an exemplary curve 10 in FIG. 1) which is expressed by the equation:

$$I = I_R * (1 + d_c/d)$$

where $I_R$ represents the current at the rheobase, i.e., the lowest current pulse (independent of duration) that can stimulate the body tissue and $d_c$ represents the chronaxie time duration, i.e., a duration at which stimulation requires twice the rheobase current value.

This relationship is readily apparent by setting d equal to $d_c$ which results in $I = 2*I_R$.

This equation can be adjusted to display voltage by multiplying each side by the lead impedance, resulting in:

$$V = V_R * (1 + d_c/d)$$

The energy used for each pulse is a function of the amplitude level (i.e., voltage or current) and the duration of the delivered pulse as shown in the equation:

$$E = (V^2 * d)/R$$

where V is the amplitude of the voltage pulse, d is its duration and R is the lead impedance.

It has been observed and can be shown that the minimum energy point on the strength-duration curve is at a chronaxie point 12 (as shown in FIG. 1 which shows a prior art implementation of a stimulation energy curve), i.e., where the amplitude component is twice the rheobase 10 and the duration component is the chronaxie duration. Known automatic capture/threshold algorithms adjust the threshold amplitude, e.g., voltage, at a fixed duration, preferably the chronaxie duration. It appears that these algorithms are based on the assumption that changes in the strength-duration curve solely effect the rheobase, i.e., if the chronaxie is essentially fixed, the strength-duration curve will solely shift vertically during the life of the patient (see curve 14 relative to curve 10). Since the known existing automatic capture/threshold algorithms only alter the amplitude component (see stimulation energy curve 16), the belief that the chronaxie is "fixed" for a given patient is inherent in these algorithms. If in fact the chronaxie is fixed, an amplitude shift alone will result in the minimum energy dissipation since the stimulation point would shift from the chronaxie point 12 of strength-duration curve 10 to the chronaxie point 18 of the subsequent strength-duration curve 14.

Additionally, it is shown in a copending, commonly assigned PCT Patent application No. SE99/00813 to Nils Holmstrom entitled "Variable Safety Margin in Autocapture Pacemakers," that due to the shape of the strength-duration curve, a larger safety margin is desirable with shorter duration stimulation pulses. Accordingly, the strength-duration curve (see FIG. 2) is divided into two regions having differently sized safety margins. The Holstrom application is incorporated herein by reference.

However, in contrast to the belief that the chronaxie was fixed, it has been noted by Raschack in an article entitled: "Differences in the cardiac actions of the calcium antagonists verapamil and nifedipine" Arzneimittelforschung 1976;26 (7):1330–3, that the strength-duration curve "is shifted to the right and the chronaxia (sic) value is significantly increased by verapamil."

The present inventors opines that such a horizontal shift, i.e., a chronaxie shift, or a combined horizontal and vertical shift, i.e., a shift in the rheobase and chronaxie, are not optimally accommodated by the prior art. Additionally, it is noted that since the energy dissipation is related to the square of the amplitude (voltage) of a stimulation pulse and only linearly related to its duration, amplitude-only increases to regain/maintain capture may be wasteful of battery capacity.

The altering of amplitude or duration have been examined in U.S. Pat. No. 5,697,956 to Bornzin, which is incorporated herein by reference. The Bornzin patent recognized that while the selection of stimulation energy levels was ideally related to the strength-duration curve for the patient's cardiac tissue, optimal increases in energy levels should also take into account the battery voltage when voltage doublers (or triplers) are necessary to achieve a desired stimulation voltage. Accordingly, the Bornzin patent shows a stimulation energy curve (see FIG. 7 of Bornzin) that selectively increased either amplitude or duration (but not both) to increase the stimulation energy level while avoiding use of the voltage doublers (or triplers) when possible. However, the Bornzin patent does not show a system in which amplitude and duration were concurrently increased to increase stimulation energy.

U.S. Pat. No. 4,590,941 to Saulson et al. did show the use of stimulation pulses where the amplitude and the pulse width components of stimulation pulses were linearly related. However, Saulson did not show the use of these pulses in a system which included a method for automatic capture/threshold determination. In fact, this amplitude/duration relationship was not used in Saulson to improve capture of the patient's heart. Specifically, Saulson disclosed a system in which its programmability was unidirectional and the only way to confirm the system's programming was to monitor the stimulation pulse's duration and thus infer the stimulation pulse's amplitude due to this predefined relationship.

Therefore what is needed is a system that can adjust the amplitude and duration of stimulation pulses to improve immunity to shifts in the strength-duration curve and thus maintain capture in an automatic capture/threshold environment while minimizing battery depletion.

SUMMARY OF THE INVENTION

The present invention provides an improved system and method for performing automatic capture and threshold detection in an implantable cardiac stimulation device. The present invention defines an essentially linear stimulation energy curve that predominantly exhibits a concomitant increase in the amplitude and duration components of the stimulation pulses to achieve and maintain capture and that has an increased immunity (i.e., a decreased susceptibility) to changes in the chronaxie and/or rheobase. Consequently, the ability to regain capture in the event of a loss-of-capture is improved because it will regain capture more quickly as well as generally reducing the required energy consumption. Additional embodiments of the present invention further alter the stimulation energy curve to accommodate the use of voltage multipliers (i.e., doublers or triplers) when necessary.

A preferred implantable cardiac stimulation device is configured for stimulating a patient's heart through at least one electrode implanted in electrical contact with selected cardiac tissue using a pulse generator configured for electrical coupling to the electrode and configured to generate stimulation pulses at a controlled energy level to thereby stimulate the patient's heart, wherein the controlled energy level is defined by a set of characteristics including an amplitude component and a duration component. Additionally, a detection circuit is configured for electrical coupling to the electrode and configured to receive cardiac signals for determining the presence or absence of an evoked response to each of the stimulation pulses. A preferred device operates under control of a controller, coupled to the pulse generator which increases the controlled energy level in response to a loss-of-capture criteria related to the absence of an evoked response. In such a case, the controlled energy level is increased from a first energy level to a second energy level where the amplitude component of the second energy level exceeds the amplitude component of the first energy level and the duration component of the second energy level exceeds the duration component of the first energy level.

In a significant aspect of the present invention, the relationship between the amplitude and duration components is defined by an essentially linear relationship specified by the equation:

$$\text{amplitude} = (\text{slope} * \text{duration}) + \text{offset}$$

where the slope is a value in amplitude units/duration units. For example, if amplitude is in volts and duration is in milliseconds, the slope is in units of volts/millisecond.

In a further aspect of the present invention, the chronaxie and rheobase of the strength-duration curve are periodically determined and the relationship between the amplitude and duration components are determined accordingly.

In a next aspect of a preferred embodiment of the present invention, the stimulation energy curve is adjusted to additionally include a portion where the amplitude component is essentially fixed and the duration component increases to minimize power consumption resulting from the use of a voltage multiplier to generate the required amplitude component.

The novel features of the invention are set forth with particularity in the appended claims. The invention will be best understood from the following description when read in conjunction with the accompanying drawings.

BRIEF DESCRIPTION OF THE DRAWINGS

FIGS. 10 and 11 show an exemplary structure of an amplitude-duration table that may be used to specify the amplitude and duration components of stimulation pulses along a defined stimulation energy curve.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention provides an improved system and method for performing automatic capture and threshold detection in an implantable cardiac stimulation device, e.g., a pacemaker or an implantable cardioverter/defibrillator (ICD).

Figure 1:
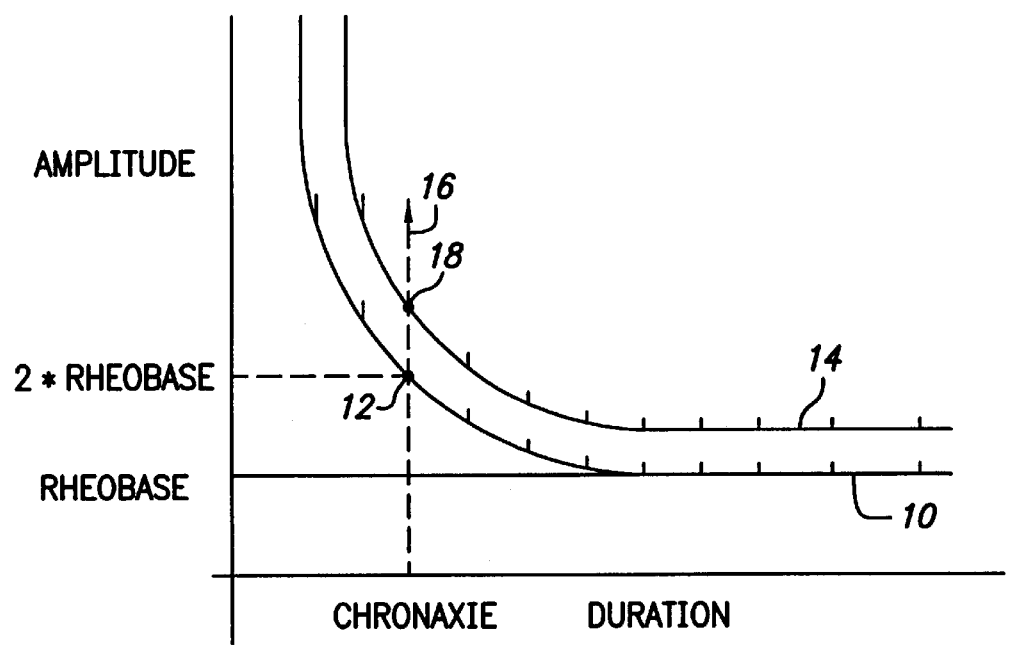
FIG. 1 is a diagram showing a pair of exemplary strength-duration curve having fixed chronaxie values and varying rheobase values that demonstrate the vertical stimulation energy adjustment curve of the prior art.
Figure 2:
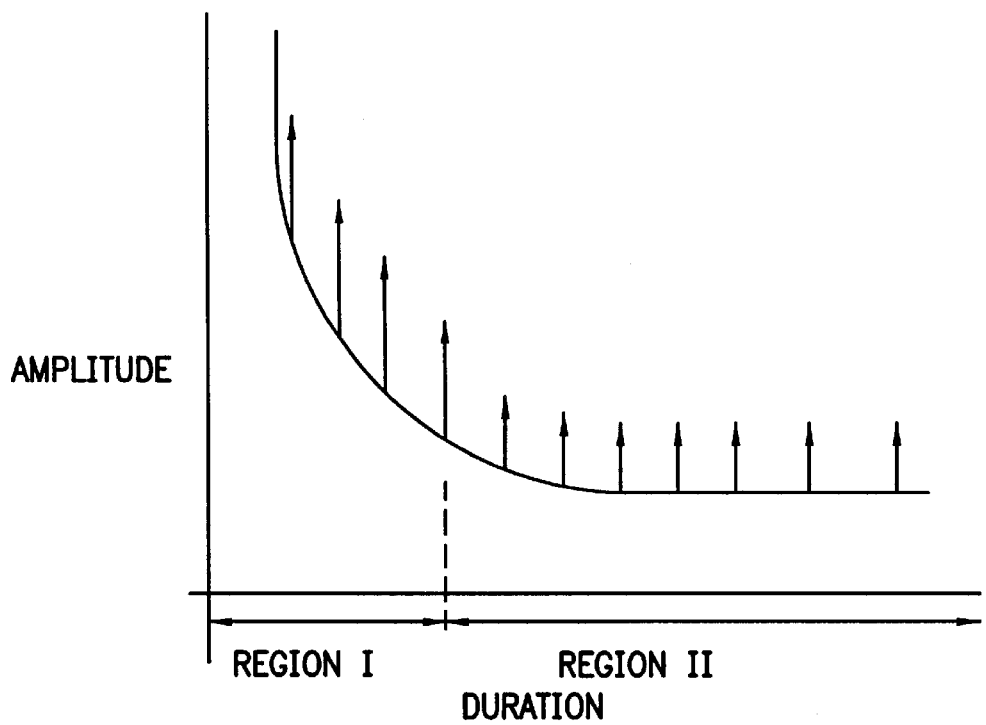
FIG. 2 shows a strength-duration curve having a safety margin that varies between two levels according to two pulse duration regions.
Figure 3:
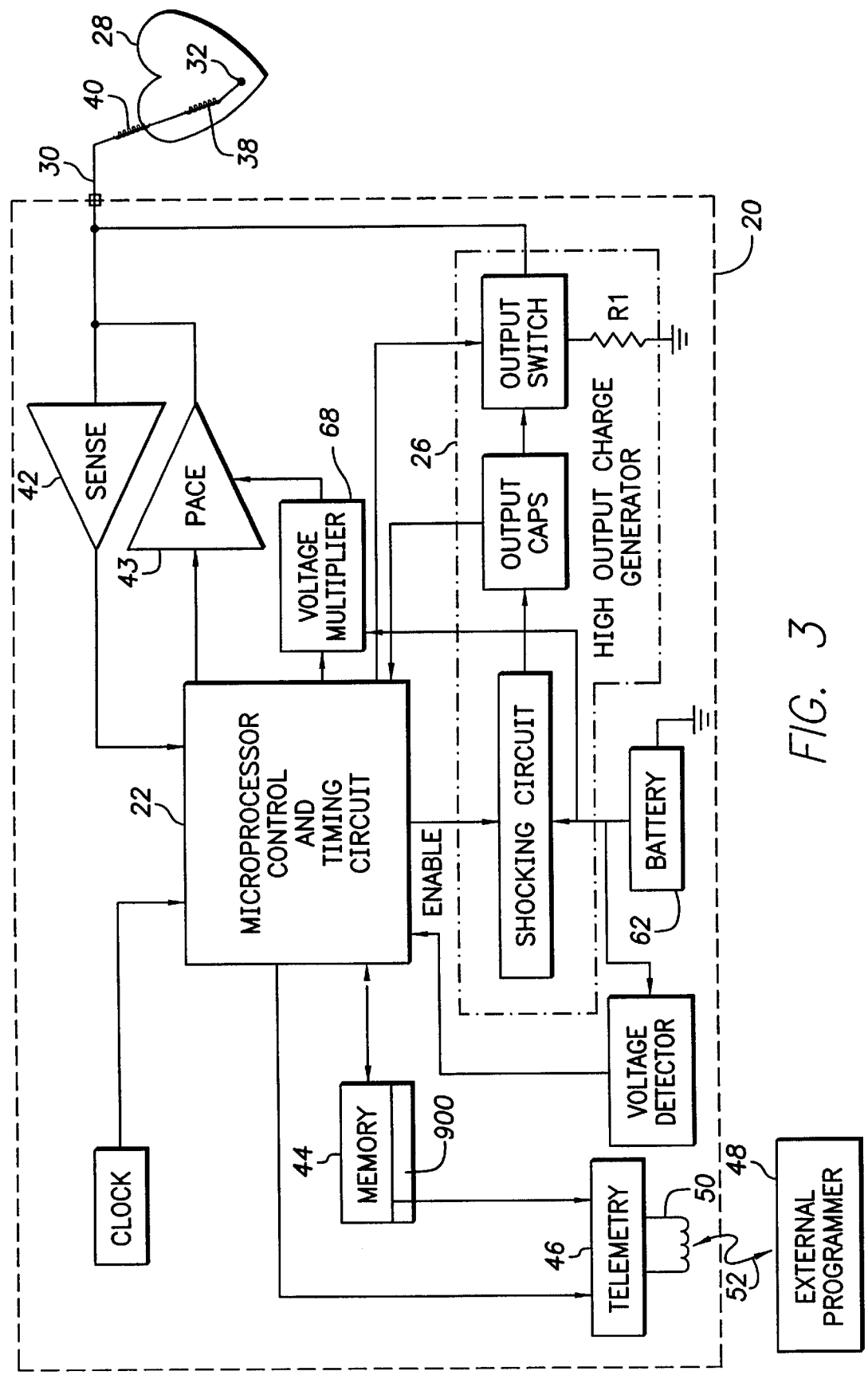
FIG. 3 shows a simplified functional block diagram of an implantable cardioverter/defibrillator (ICD), which represents one type of implantable cardiac stimulation device with which the present invention may be used.
Figure 4:
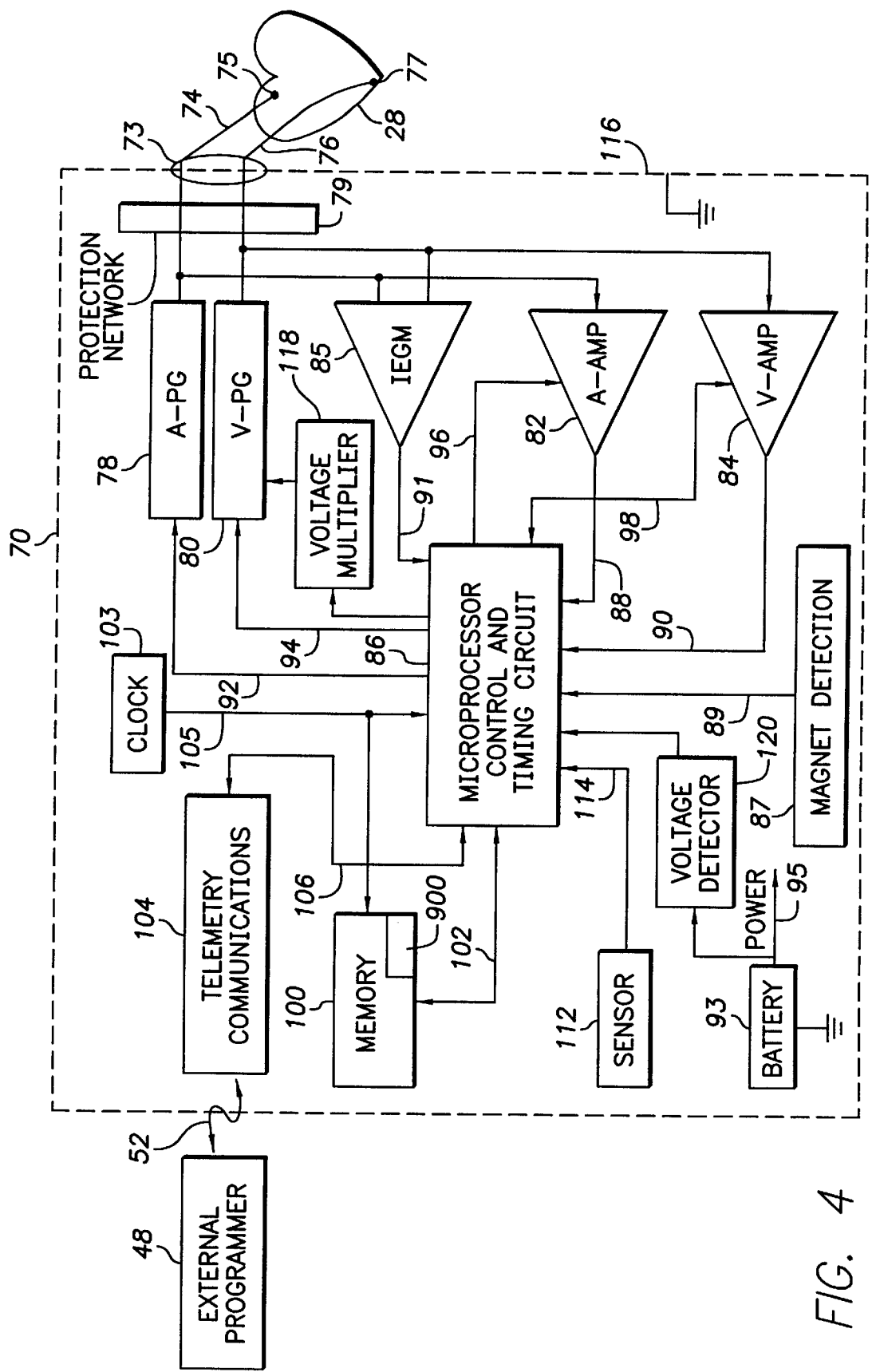
FIG. 4 shows a functional block diagram of an implantable dual-chamber pacemaker, which represents another type of implantable medical device with which the invention may be used.

To better understand the invention, it will first be helpful to have an understanding of the basic functions performed by exemplary implantable stimulation devices with which the invention may be used, e.g., an ICD with dual chamber coils (see FIG. 3) and/or a dual-chamber pacemaker (see FIG. 4). While a dual-chamber device has been chosen for this description, this is for teaching purposes only. It is recognized that the present invention could be implemented into a device having one to four chambers, that one of skill in the art could readily adapt the dual-chamber device shown in FIG. 4 to perform single or multiple-chamber functionality, and that a single or multiple chamber device is within the spirit of the invention as is any device capable of delivering stimulating impulses to a tissue or organ of the body.

In FIG. 3, there is shown a simplified functional block diagram of an ICD device 20, and in FIG. 4, there is shown a simplified functional block diagram of a dual-chamber pacemaker 70. It should also be noted that, in some instances, the functions of an ICD and a pacemaker may be combined within the same cardiac stimulation device. However, for teaching purposes, the devices will be described separately.

It is the primary function of an ICD device to sense the occurrence of a tachyarrhythmia and to automatically apply an appropriate electrical shock therapy to the heart aimed at terminating the tachyarrhythmia. To this end, the ICD device 20, as shown in the functional block diagram of FIG. 3, includes a control and timing circuit (hereinafter referred to as a control/timing circuit) 22, such as a microprocessor, state-machine or other such control circuitry, that controls a high output charge generator 26. The high output charge generator 26 generates electrical stimulation pulses of moderate or high energy (corresponding to cardioversion or defibrillation pulses, respectively), e.g., electrical pulses having energies of from 1 to 10 joules (moderate) or 11 to 40 joules (high), as controlled by the control/timing circuit 22.

Such moderate or high energy pulses are applied to the patient's heart 28 through at least one lead 30 having at least two defibrillation electrodes, such as coil electrodes 38 in the atrium and 40 in the superior vena cava. The lead 30 preferably also includes at least one electrode for pacing and sensing functions, such as electrode 32. Typically, the lead 30 is transvenously inserted into the heart 28 so as to place the coil electrodes 38 and 40 where they are in electrical and preferably physical contact with the patient's heart 28. While only one lead is shown in FIG. 3, it is to be understood that additional defibrillation leads and electrodes may be used to apply the shock treatment generated by the high voltage generator 26 to the patient's heart 28.

The ICD 20 also includes a sense amplifier 42 that is coupled to at least one sensing electrode 32. It is the function of the sense amplifier 42 to sense the electrical activity of the heart 28, as is known in the art, such as R-waves which are the surface ECG representation of ventricular depolarizations which result in the contraction of ventricular tissue, and P-waves which are the surface ECG manifestations of atrial depolarizations which result in the contraction of atrial tissue. Thus, by sensing the ventricular and/or atrial depolarizations (manifested by the R-waves and/or P-waves on the surface ECG) through the sense amplifier 42, the control/timing circuit 22 is able to make a determination as to the rate and regularity of the patient's heart beat. Such information, in turn, allows the control/timing circuit 22 to determine whether the patient's heart 28 is experiencing an arrhythmia, and to apply appropriate stimulation therapy. Alternatively, a pacing pulse generator 43 can be used to pace the heart in accordance with a preselected pacing strategy. To accomplish this task, the amplitude of pacing pulses generated by the pulse generator 43 is set by the physician to a value above the threshold level, e.g., by a fixed value, for the patient's heart to ensure capture, i.e., successful stimulation of the patient's heart.

The control/timing circuit 22 further has a memory circuit 44 coupled thereto wherein the operating parameters used by the control/timing circuit 22 are stored. Such operating parameters define, for example, the amplitude of each shocking pulse to be delivered to the patient's heart 28 as well as the duration of these shock pulses. The memory 44 may take many forms, and may be subdivided into as many different memory blocks or sections (addresses) as needed to store desired data and control information. A feature of an exemplary ICD 20 is the ability to sense and store a relatively large amount of data as a data record, which data record may then be used to guide the operation of the device, i.e., the present operating mode of the device may be dependent, at least in part, on past performance data.

Advantageously, the operating parameters of the implantable device 20 may be non-invasively programmed into the memory 44 through a telemetry circuit 46, in telecommunicative contact with an external programmer 48 by way of a suitable coupling coil 50. The coupling coil 50 may serve as an antenna for establishing a radio frequency (RF) communication link 52 with the external programmer 48, or the coil 50 may serve as a means for inductively coupling data between the telemetry circuit 46 and the external programmer 48, as is known in the art. See, e.g., U.S. Pat. Nos. 4,809,697 (Causey, III et al.) and U.S. Pat. No. 4,944,299 (Silvian), incorporated herein by reference. Further, such telemetry circuit 46 advantageously allows status information relating to the operation of the ICD 20, as contained in the control/timing circuit 22 or memory 44, to be sent to the external programmer 48 through the established link 52.

The control/timing circuit 22 includes appropriate processing and logic circuits for analyzing the output of the sense amplifier 42 and determining if such signals indicate the presence of an arrhythmia. Typically, the control/timing circuit 22 is based on a microprocessor, controller, or similar processing circuit, which includes the ability to process or monitor input signals (data) in a prescribed manner, e.g., as controlled by program code stored in a designated area or block of the memory 44. The details of the design and operation of the control/timing circuit 22 are not critical to the present invention. Rather, any suitable control/timing circuit 22 may be used that performs the functions described herein. The use, design, and operation of microprocessor-based control circuits to perform timing and data analysis functions is known in the art.

The ICD 20 additionally includes a battery 62 which provides operating power to all of the circuits of the ICD 20. The battery 62 additionally provides power to a voltage multiplier 68, e.g., a voltage doubler or tripler, which operates under control of the control timing circuit 22 when necessary for providing stimulation voltages in excess of the battery voltage.

In FIG. 4, a simplified block diagram of the circuitry needed for a dual-chamber pacemaker 70 is illustrated. The pacemaker 70 is coupled to heart 28 by way of leads 74 and 76, the lead 74 having an electrode 75 that is in electrical and preferably physical contact with one of the atria of the heart 28, and the lead 76 having an electrode 77 that is in electrical and preferably physical contact with one of the ventricles of the heart 28. The leads 74 and 76 are electrically and physically connected to the pacemaker 70 through a connector 73 that forms an integral part of the housing wherein the circuits of the pacemaker are housed. Typically, leads 74 and 76 are operated in a bipolar mode where a "tip" portion provides the voltage signal that provides current that flows to a "ring" portion on the same lead. Alternatively, leads 74 and 76 can operate in a unipolar mode where current flows from the "tip" portion of each lead to a conductive case 116 which surrounds the pacemaker device 70.

The connector 73 is electrically connected to a protection network 79, which network 79 electrically protects the circuits within the pacemaker 70 from excessive shocks or voltages that could appear on the electrodes 75 and/or 77 in the event such electrodes were to come in contact with a high voltage signal, e.g., from a defibrillation shock.

The leads 74 and 76 carry stimulation pulses to the electrodes 75 and 77 from an atrial pulse generator (A-PG) 78 and a ventricular pulse generator (V-PG) 80, respectively. Further, electrical signals from the atria are carried from the electrode 75, through the lead 74, to the input terminal of an atrial channel sense amplifier (A-AMP) 82; and electrical signals from the ventricles are carried from the electrode 77, through the lead 76, to the input terminal of a ventricular channel sense amplifier (V-AMP) 84. Similarly, electrical signals from both the atria and ventricles are applied to the inputs of an intracardiac electrogram amplifier (IEGM) 85. The amplifier 85 is typically configured to detect an evoked response from the heart 28, i.e., a response to an applied stimulation pulse, thereby aiding in the detection of "capture". Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue. Following each captured stimulation pulse, the associated cardiac tissue (i.e., the atria or the ventricles) enters into a physiologic refractory period during which it cannot be re-stimulated.

The dual-chamber pacemaker 70 is controlled by a control and timing circuit (hereinafter referred to as a control/timing circuit) 86 that typically includes a microprocessor programmed to carry out control and timing functions. The control/timing circuit 86 receives the sensed signals from the atrial (A-AMP) amplifier 82 over signal line 88. Similarly, the control/timing circuit 86 receives the output signals from the ventricular (V-AMP) amplifier 84 over signal line 90, and the output signals from the IEGM amplifier 85 over signal line 91. These output signals which indicate capture due to an evoked response are generated each time that a P-wave or an R-wave is sensed within the heart 28. The control/timing circuit 86 also generates trigger signals that are sent to the atrial pulse generator (A-PG) 78 and the ventricular pulse generator (V-PG) 80 over signal lines 92 and 94, respectively, to control the amplitude and duration of the signals delivered to the electrodes, 75 and 77. These trigger signals are generated each time that a stimulation pulse is to be generated by the respective pulse generator 78 or 80. The atrial trigger signal is referred to simply as the "A-trigger", and the ventricular trigger signal is referred to as the "V-trigger".

During the time that either an A-pulse or V-pulse is being delivered to the heart, the corresponding sense amplifier, A-AMP 82 and/or V-AMP 84, is typically disabled by way of a blanking signal presented to these amplifiers from the control/timing circuit 86 over signal lines 96 and 98, respectively. This blanking action prevents the amplifiers 82 and 84 from becoming saturated from the relatively large stimulation pulses that are present at their input terminals during this time. This blanking action also helps prevent residual electrical signals present in the muscle tissue as a result of the pacemaker stimulation from being interpreted as P-waves or R-waves.

As shown in FIG. 4, the pacemaker 70 further includes a memory circuit 100 that is coupled to the control/timing circuit 86 over a suitable data/address bus 102. This memory circuit 100 allows certain control parameters, used by the control/timing circuit 86 in adjusting or programming the operation of the pacemaker 70, to be stored and modified, as required, in order to customize the pacemaker's operation to suit the needs of a particular patient. Further, data regarding the operation of the pacemaker 70 (sensed or paced events and activation of any special algorithms or results of interventions) may be stored in the memory 100 for later retrieval and analysis.

As with the memory 44 of the ICD device 20 shown in FIG. 3, the memory 100 of the pacemaker 70 (FIG. 4) may take many forms and may be subdivided into as many different memory blocks or sections (addresses) as needed in order to allow desired data and control information to be stored. A feature of an exemplary cardiac stimulation device is the ability to store a relatively large amount of sensed data as a data record, which data record may then be used to guide the operation of the device. That is, the operating mode of the pacemaker may be dependent, at least in part, on past performance data. For example, an average atrial rate may be determined based on the sensed atrial rate over a prescribed period of time. This average rate may then be stored and updated at regular intervals. Such stored rate may then be compared to a present atrial rate and, depending upon the difference, used to control the operating mode of the pacemaker. Other parameters, of course, in addition to (or in lieu of) atrial rate, may be similarly sensed, stored, averaged (or otherwise processed), and then used for comparison purposes against one or more currently-sensed parameters. Advantageously, modern memory devices allow for the storage of large amounts of data in this manner.

A clock circuit 103 directs an appropriate clock signal(s) to the control/timing circuit 86, as well as to any other needed circuits throughout the pacemaker 70 (e.g., to the memory 100) by way of clock bus 105.

A telemetry/communications circuit 104 is further included in the pacemaker 70. This telemetry circuit 104 is connected to the control/timing circuit 86 by way of a suitable command/data bus 106. In turn, the telemetry circuit 104, which is included within the implantable pacemaker 70, may be selectively coupled to the external programmer 48 by means of the communication link 52. The communication link 52 may be any suitable electromagnetic link such as an RF (radio frequency) channel, a magnetic link, an inductive link, an optical link, and the like. Advantageously, desired commands may be sent to the control/timing circuit 86 through the external programmer 48 and the communication link 52. Similarly, through this communication link 52 with the programmer 48, data commands (either held within the control/timing circuit 86, as in a data latch, or stored within the memory 100) may be remotely received from the programmer 48. Similarly, data initially sensed through the leads 74 or 76, and processed by the control/timing circuit 86, or other data measured within or by the pacemaker 70, may be stored and uploaded to the programmer 48. In this manner, non-invasive communications can be established with the implanted pacemaker 70 from a remote, non-implanted, location.

The pacemaker 70 additionally includes a battery 93 which provides operating power to all of the circuits of the pacemaker 70 via a power signal line 95. The battery 93 additionally provides power to a voltage multiplier 118, e.g., a voltage doubler or tripler, which operates under control of the control/ timing circuit 86 when necessary for providing stimulation voltages in excess of the battery voltage.

It is noted that the pacemaker 70 in FIG. 4 is referred to as a dual-chamber pacemaker because it interfaces with both the atria and the ventricles of the heart 28. Those portions of the pacemaker 70 that interface with the atria, e.g., the lead 74, the P-wave sense amplifier 82, the atrial pulse generator 78, and corresponding portions of the control/timing circuit 86, are commonly referred to as the "atrial channel". Similarly, those portions of the pacemaker 70 that interface with the ventricles, e.g., the lead 76, the R-wave sense amplifier 84, the ventricular pulse generator 80, and corresponding portions of the control/timing circuit 86, are commonly referred to as the "ventricular channel". While a dual chamber pacemaker includes a single atrial channel and a single ventricular channel, multichamber devices may include more than one atrial channel and/or more than one ventricular channel.

As needed for certain applications, the pacemaker 70 may further include at least one sensor 112 that is connected to the control/timing circuit 86 of the pacemaker 70 over a suitable connection line 114. While this sensor 112 is illustrated in FIG. 4 as being included within the pacemaker 70, it is to be understood that the sensor may also be external to the pacemaker 70, yet still be implanted within or carried by the patient. A common type of sensor is an activity sensor, such as a piezoelectric crystal, that is mounted to the case of the pacemaker. Other types of sensors are also known, such as sensors that sense the oxygen content of blood, respiration rate, pH of blood, body motion, and the like. The type of sensor used is not critical to the present invention. Any sensor or combination of sensors capable of sensing a physiological or physical parameter relatable to the rate at which the heart should be beating (i.e., relatable to the metabolic need of the patient), and/or relatable to whether a tachyarrhythmia is likely to soon occur, can be used. Such sensors are commonly used with "rate-responsive" or "rate-modulated" pacemakers in order to adjust the rate (pacing cycle) of the pacemaker in a manner that tracks the physiological or metabolic needs of the patient.

The pacemaker 70 further includes magnet detection circuitry 87, coupled to the control/timing circuit 86 over signal line 89. It is the purpose of the magnet detection circuitry 87 to detect when a magnet is placed over the pacemaker 70. The magnet may be used by a physician or other medical personnel to perform various reset functions of the pacemaker 70 and/or to signal the control/timing circuit 86 that an external programmer 48 is in place to receive data from, or send data to, the pacemaker memory 100 or control/timing circuit 86 through the telemetry communications circuit 104.

As with the ICD device 20 of FIG. 3, the telemetry or communications circuit 104 may be of conventional design, such as is described in U.S. Pat. No. 4,944,299, or as is otherwise known in the art. Similarly, the external programmer 48 may be of any suitable design known in the art, such as is described in U.S. Pat. No. 4,809,697. Likewise, the memory circuit 100, and the circuits utilized in the atrial and ventricular channels may all be of common design as is known in the pacing art. The present invention is not concerned with the details of the circuitry utilized for each of these pacing elements. Rather, it is concerned with the manner in which the amplitude and the duration (width) of the pacing pulses delivered to the heart are determined in coordination with automatic capture and threshold modes of operation. Such determination is controlled by the control/timing circuit 86.

The control/timing circuit 86 may be realized using a variety of different techniques and/or circuits as known in the art. The preferred type of control/timing circuit 86 is a microprocessor-based control/timing circuit. It is noted, however, that the control/timing circuit 86 could also be realized using, for example, a state machine. Indeed, any type of control/timing circuit, controller or system could be employed for the control/timing circuit 86. The present invention is likewise not concerned with the details of the control/timing circuits 22 and 86. Rather, it is concerned with the end result achieved by the control/timing circuit. That is, so long as the control/timing circuit 86 controls the operation of the pacemaker (or other medical device) so that the desired functions are achieved as set forth herein, it matters little what type of control/timing circuit is used. Those of skill in the implantable medical device art, given the teachings presented herein, should thus be able to fashion numerous different types of control/timing circuits that achieve the desired device control.

Representative of the types of control/timing circuits that may be used with the invention is the microprocessor-based control/timing circuit described in U.S. Pat. No. 4,940,052, entitled "Microprocessor Controlled Rate-Responsive Pacemaker Having Automatic Rate Response Threshold Adjustment". Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298 and '980 patents are incorporated herein by reference.

Figure 5:
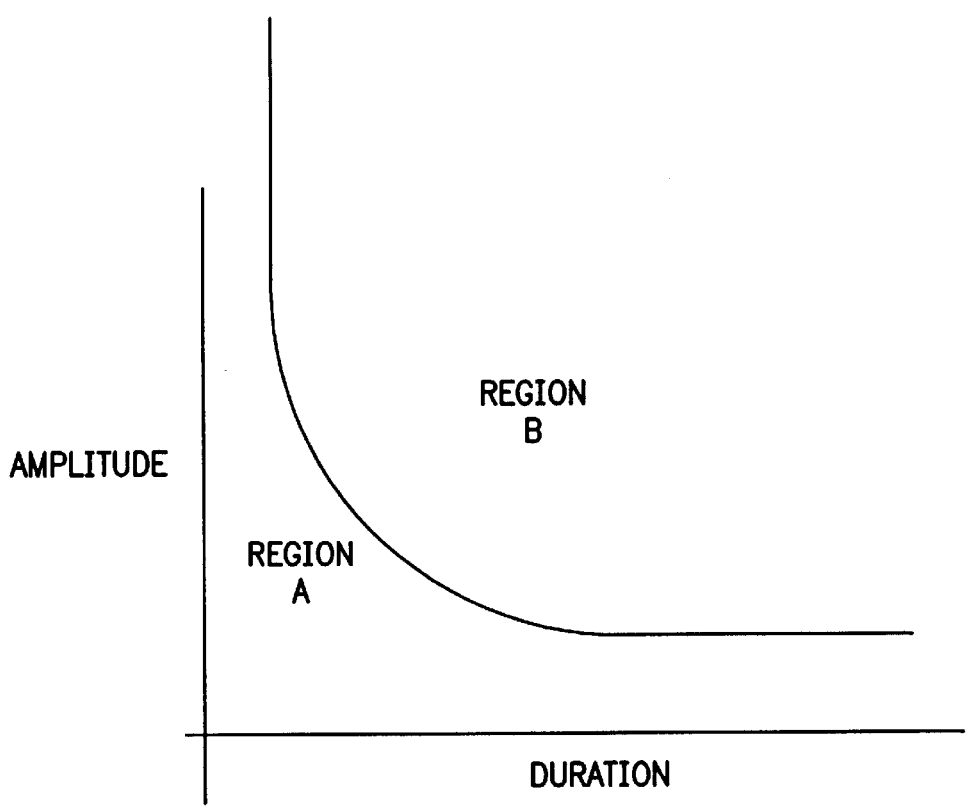
FIG. 5 shows an exemplary strength-duration curve and the regions where capture does and does not occur.

The strength-duration curve described by Lapicque teaches that the ability to depolarize, i.e., cause a muscle to contract, is a function of both the amplitude and duration of a stimulation pulse and not just the overall energy level. For example, if a stimulation pulse is provided with an amplitude below the rheobase but at infinite duration (and thus infinite energy), the muscle will still not be stimulated. Similarly, if a stimulation pulse is provided with an extremely large amplitude but at a very small duration, there will be no stimulation. Graphically, it may be seen that points below (i.e., downward and to the left) the strength-duration curve (see Region A of FIG. 5) will not result in stimulation and that points above (i.e., upward and to the right) or on the strength-duration curve will result in stimulation (see Region B of FIG. 5). Furthermore, it is believed that increasing the graphical distance (i.e., the graphically viewed variation in amplitude and duration as will be shown in reference to FIG. 8) of a stimulation energy point away from the strength-duration curve in Region B increases the immunity (i.e., decreases the susceptibility) of the system to measurement and stimulation pulse variations and variations in the chronaxie and rheobase which will reposition the strength-duration curve.

Figure 6:
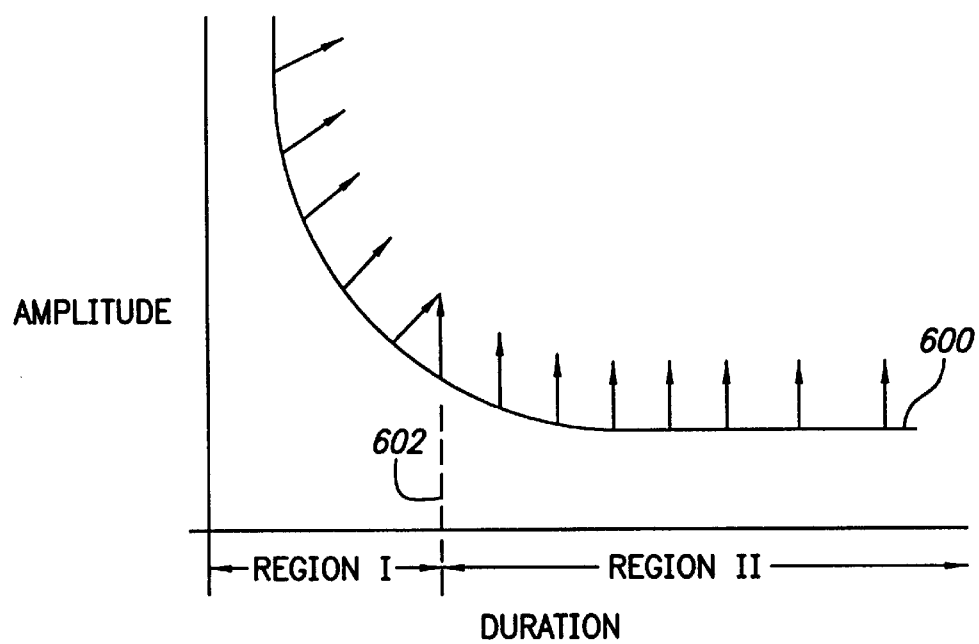
FIG. 6 shows a strength-duration curve where a plurality of essentially linear stimulation energy curves are defined for two pulse duration regions where the stimulation energy curves are angular in a first region and vertical in a second region.

Accordingly, in a first embodiment of the present invention as shown in FIG. 6, it is observed that the strength-duration curve 600 is relatively flat in Region II, i.e., the pulse duration region above a first duration threshold 602, e.g., the chronaxie duration. Accordingly, the maximum immunity to variations is achieved by solely increasing the amplitude of stimulation pulses in Region II since the relative effect of duration increases are minimal. However, in Region I, i.e., the pulse duration region below the first duration threshold 602, the immunity is preferably increased by increasing both the amplitude and duration components or, in an alternative embodiment, increasing the duration component by one step (as a minimum) while the amplitude increases can range from 0–2 steps, for example. The first duration threshold 602 may be predefined, programmable via the external programmer 48, or, as discussed further below, the chronaxie (and rheobase) may be periodically calculated and this calculated chronaxie value (or a value related to this value) may be used as the first duration threshold 602.

Figure 7:
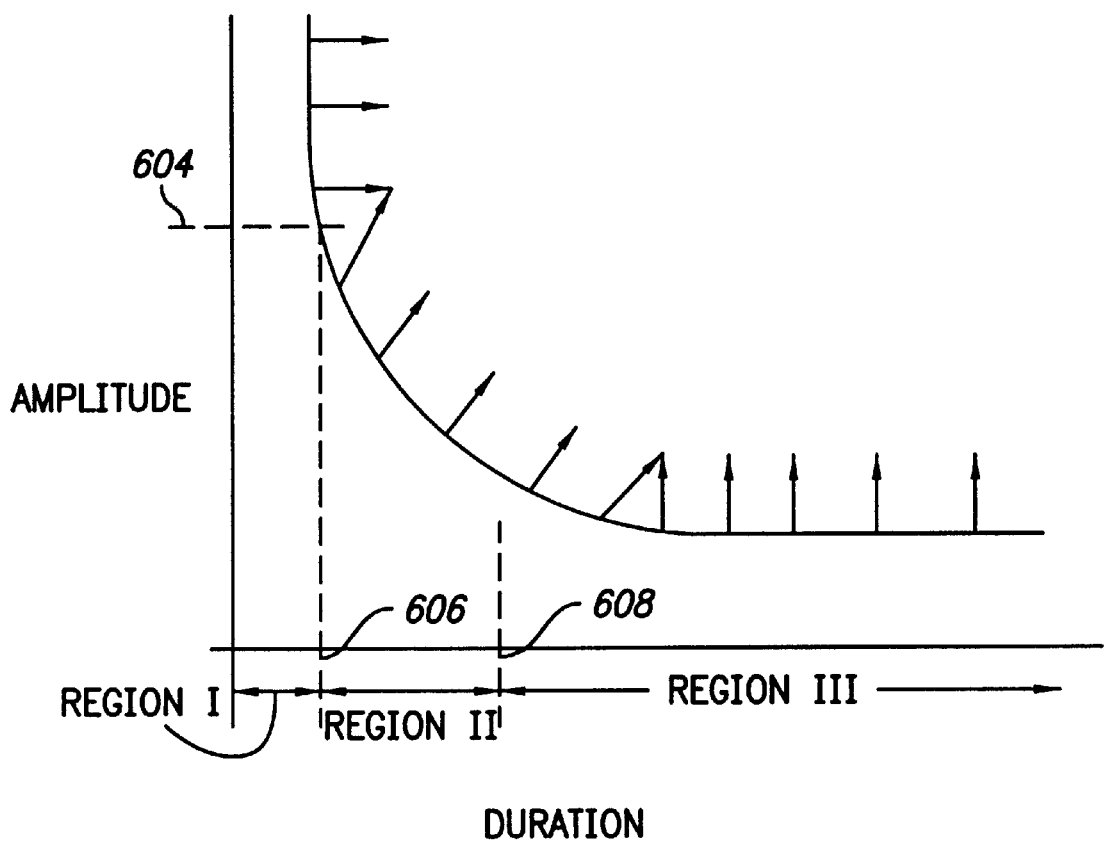
FIG. 7 shows a strength-duration curve where a plurality of essentially linear stimulation energy curves are defined for three regions where the stimulation energy curves are horizontal in a first region, angular in a second region and vertical in a third region.

In a second embodiment of the present invention as shown in FIG. 7, it is further observed that there is little consequence of increasing the amplitude in Region I due to the predominantly vertical slope of the strength-duration curve within that region. Accordingly, increases in stimulation energy in Region I predominantly occur by increasing the pulse duration. Region I may be defined by an amplitude threshold 604. For example, the amplitude threshold 604 may be a value related to the rheobase value, e.g., 3*rheobase, or may be defined by a second duration threshold 606, e.g., 0.5*chronaxie. In Region III, in a manner similar to that previously described for Region II in FIG. 6, the stimulation energy is increased by predominantly increasing the amplitude component. Region III is defined by a third duration threshold 608, e.g., a value 50% greater than the chronaxie duration. In Region II, both the amplitude and duration components are increased, preferably linearly, as previously described in relationship to Region I in FIG. 6. As previously described, these thresholds may be predefined, programmable from the external programmer 48 or may be automatically set as a result of a periodic chronaxie/rheobase calculation.

Figure 8:
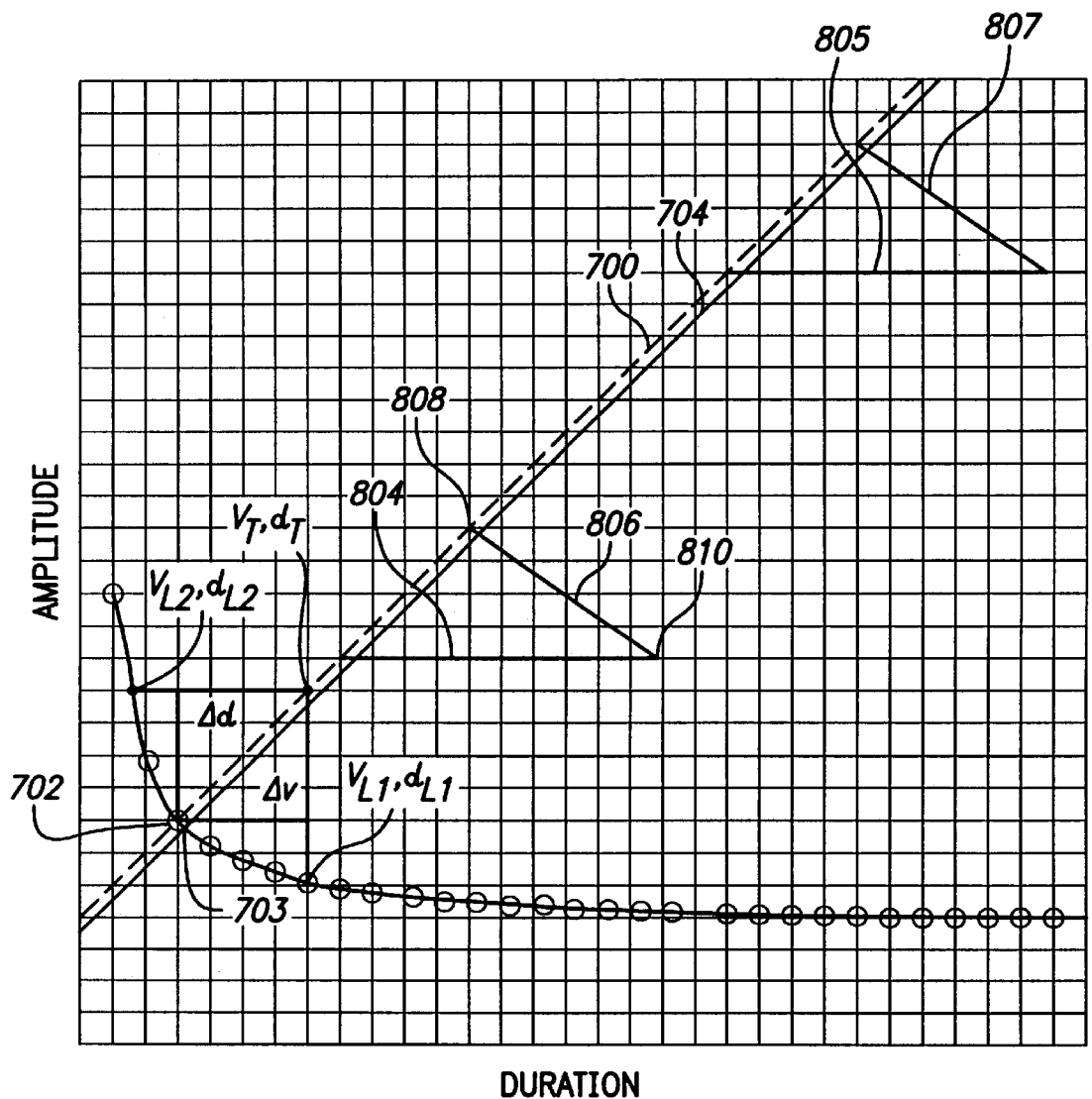
FIG. 8 shows a graphical description of an alternative stimulation energy curve of the present invention.

A third embodiment, graphically illustrated in FIG. 8, incorporates all of the prior reasoning in a single, optimal solution. It is believed that a stimulation energy curve that is equidistant from all points on the strength-duration curve will present the maximum immunity (i.e., minimized susceptibility) to measurement and stimulation pulse variations and variations in the chronaxie and rheobase which will reposition the strength-duration curve. In a first variation, this stimulation energy curve (see stimulation energy curve 700) intersects the strength-duration curve at its chronaxie point 702 so that the lowest energy capture point of the strength-duration curve and the lowest energy capture point of the stimulation energy curve coincide. At this intersection point, the distance of the stimulation energy curve from the strength-duration curve will be, by definition, zero in amplitude and in duration.

Stimulation energy curve 700 (see FIG. 8 which graphs amplitude in volts vs. duration in milliseconds) has a differential increase in amplitude (e.g., voltage $V_T$ in volts) and duration $d_T$ (in milliseconds) equal to each other at all points on the stimulation energy curve. Thus, for a unity slope:

$$\Delta V = \Delta d$$

$$\Delta V = V_T - V_C = d_T - d_C$$

where $V_C$ is the voltage at the chronaxie duration ($d_c$) which is, by definition, twice the rheobase ($V_R$). Thus, $$\Delta V = V_T - (2*V_R) = d_T - d_C$$

Thus, $$V_T = d_T + ((2*V_R) - d_C) \quad \text{Equation 1}$$

i.e., the preferred stimulation energy curve is represented by an equation of the form:

amplitude=(slope*duration)+offset where the slope is preferably 1.0 volts/millisecond and the offset value (in volts) is preferably:

(2*rheobase)−chronaxie where the rheobase value is in volts and the chronaxie value is in milliseconds.

This stimulation energy curve presumes an ideal stimulation pulse generator (i.e., a pulse generator that is not subject to quantization effects) and a strength-duration curve that is equally susceptible to chronaxie and rheobase variations. To accommodate departures from these presumptions, the slope of a preferred stimulation energy curve may be within the range of 0.3 to 3.0 volts/millisecond. Furthermore, to accommodate actual variations in the strength-duration curve, that slope may be adjusted according to measured trends in the strength-duration curve, i.e., measured variations in the chronaxie and/or rheobase between two or more measurements.

However, it has been determined that the chronaxie point 702 is not the graphical center of the strength-duration curve and that the graphical center of the strength-duration curve is slightly to the right of the actual chronaxie point 702. This point will be referred to as a quasi-chronaxie point 703 since it bears some resemblance to the chronaxie point but is materially different in that it has been selected for its graphical significance, despite not being the minimum energy point on the strength-duration curve. In a second variation, a stimulation energy curve 704 passes through this quasi-chronaxie point 703. Stimulation energy curve 704 may be represented by the equation (where amplitude and rheobase are in units of volts and duration is in units of milliseconds, i.e., its slope of 1.0 is in units of volts/millisecond):

amplitude=duration+rheobase    Equation 2

While this stimulation energy curve 704 will not provide the minimum stimulation energy at its intersection with the strength-duration curve (since it will not intersect the actual chronaxie point 702), it will bisect the strength-duration curve and thus more accurately represent a stimulation energy curve that is equidistant from the strength-duration curve.

Figure 9:
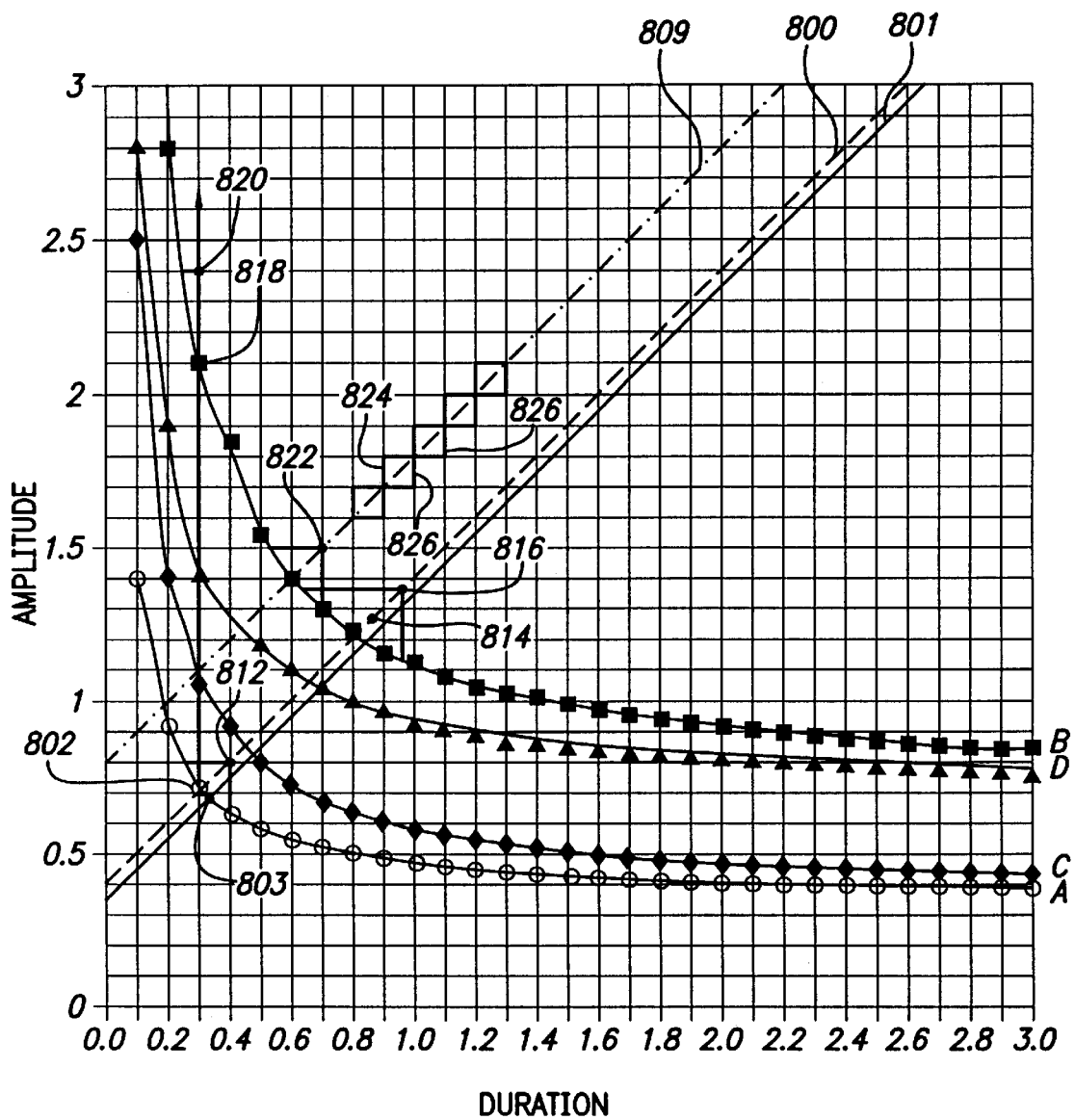
FIG. 9 shows a series of strength-duration curves having varying chronaxie values and rheobase values and a stimulation energy curve that is optimized for physiological variation and noise immunity, i.e., a minimized susceptibility to variations in chronaxie and/or rheobase as well as measurement variations.

FIG. 9 shows the use of this stimulation energy curve on a range of varying strength-duration curves having the following attributes (assuming a 500 ohm lead impedance):

| CURVE | Chronaxie (milliseconds) | Rheobase (volts) |
|---|---|---|
| A | 0.30 | 0.35 |
| B | 0.60 | 0.70 |
| C | 0.60 | 0.35 |
| D | 0.30 | 0.70 |

Strength-duration curve A is presumed to be the initial strength-duration curve for this analysis and curves B–D are exemplary variations that may occur during the operation of the cardiac stimulation device due to physiological variations. Accordingly, the stimulation energy curve 800 corresponding to the strength-duration curve A (with $V_T$ in volts and $d_T$ in milliseconds) is defined by (see Equation 1):

$$V_T = d_T + 0.40$$

Initially, it may be noted graphically that the shortest graphical distance between the chronaxie 802 of curve A, the initial chronaxie point, and the stimulation threshold of any of the other curves is along the stimulation energy curve 800. Thus, a first consequence of this stimulation energy curve is that should capture be lost, it will be able to be regained in a minimal period of time. This will limit the need for backup pulses which dissipate a "large" amount of power and may cause discomfort to some patients.

The following tables illustrate the energy effects of regaining capture along the preferred stimulation energy curve as opposed to the prior art which used a unidirectional, i.e., amplitude or pulse width only, stimulation energy curve. While energy is shown in the following tables, this is for illustration purposes only since the present invention does not require energy calculations to perform its function.

TABLE 1

Transition from curve A to curve B
(double the rheobase and double the chronaxie)

|  | Amplitude (volts) | Duration (milliseconds) | Energy (micro joules) |
|---|---|---|---|
| Chronaxie A | 0.7 | 0.3 | 0.294 |
| Chronaxie B | 1.4 | 0.6 | 2.352 |
| Preferred Curve | 1.215 | 0.815 | 2.406 |
| Prior Art | 2.1 | 0.3 | 2.646 |

In this example, the present invention will save approximately 9% in energy per pulse and will recapture faster.

TABLE 2

Transition from curve A to curve C
(double the chronaxie only with a constant rheobase)

|  | Amplitude (volts) | Duration (milliseconds) | Energy (micro joules) |
|---|---|---|---|
| Chronaxie A | 0.7 | 0.3 | 0.294 |
| Chronaxie C | 0.7 | 0.6 | 0.588 |
| Preferred Curve | 0.834 | 0.434 | 0.604 |
| Prior Art | 1.05 | 0.3 | 0.662 |

In this example, the present invention will save approximately 9% in energy per pulse and will recapture faster.

TABLE 3

Transition from curve A to curve D
(double the rheobase only with a constant chronaxie)

| | Amplitude (volts) | Duration (milliseconds) | Energy (micro joules) |
|---|---|---|---|
| Chronaxie A | 0.7 | 0.3 | 0.294 |
| Chronaxie D | 1.4 | 0.3 | 1.176 |
| Preferred Curve | 1.032 | 0.632 | 1.346 |
| Prior Art | 1.4 | 0.3 | 1.176 |

In this example, the present invention will use approximately 14% more energy per pulse. However, it will recapture faster.

Accordingly, as expected, in an environment where the chronaxie is constant, the present invention will recapture faster at the cost of some additional energy dissipation. However, in other environments, the present invention will recapture faster and save energy. Most significantly, the ability to retain capture at a given energy level will be optimized in the present invention since stimulation pulses will be selected that increase immunity to measurement variations, both amplitude and duration variations of the stimulation pulses, and variations in the strength-duration curve caused by variations in the rheobase and/or chronaxie.

In embodiments of the present invention, the stimulation energy is increased, when necessary along the stimulation energy curve. Increases in stimulation energy may be made at predetermined distances along the stimulation energy curve 800. Alternatively, the stimulation energy increases may be made in predetermined increments of energy, predetermined increments in amplitude, predetermined increments in duration, etc. These calculations may be made "on the fly" by the control/timing circuit 86.

Alternatively, a table 900, as shown in FIGS. 10 and 11, may be pre-populated by pairs of amplitude/duration components values for a range of energy values according to the previously described equations, respectively Equations 1 and 2. For example, FIG. 10 is prepopulated according to the equation:

amplitude=duration+0.40 and FIG. 11 is prepopulated according to the equation:

amplitude=duration+0.35 where amplitude is in volts and duration is in milliseconds.

FIG. 10 shows exemplary data according to the equation for the stimulation energy curve corresponding to the strength-duration curve A for a stimulation energy curve that intersects the chronaxie point 802 while FIG. 11 shows exemplary data for an alternative stimulation energy curve 801 that intersects the quasi-chronaxie point 803. In the case of FIG. 10, the chronaxie point 802 may be used as a starting controlled energy level and this energy level may be adjusted upwards by a safety margin to determine an initial controlled energy level.

Alternatively, in the case of FIG. 11, the quasi-chronaxie point 803 may be used as the starting controlled stimulation energy level. This data may be generated in advance at or by the external programmer 48 and downloaded into the table 900 or may be periodically generated by the control/timing circuit 86. The rheobase and chronaxie values may be manually entered at the external programmer and these values may be used in determining the data in table 900. Preferably, as described further below, the rheobase and chronaxie may be periodically calculated by embodiments of the present invention. Thus, the preferred stimulation energy curve can be recalculated following this periodic determination, e g., as background operation of the control/timing circuit.

A first alternative technique for determining the chronaxie and rheobase will now be described.

An equation for approximating then relationship between amplitude and duration for stimulating body, e.g., cardiac, tissue was defined in 1909 by Lapicque as a strength-duration curve. The Lapicque equation is:

$$I=I_R*(1+d_c/d)$$

where $I_R$ represents the current at the rheobase, i.e., the lowest current signal, independent of duration that can stimulate the body tissue and $d_c$ represents the chronaxie time duration, i.e., a duration at which stimulation occurs at twice the rheobase value.

This relationship is readily apparent by setting d equal to $d_c$ which results in the equation:

$$I=2*I_R$$

This equation can be adjusted to display voltage by multiplying each side by the lead impedance, resulting in:

$$V=V_R*(1+d_c/d)$$

The chronaxie and rheobase may be calculated using the present device. As described below, this calculation may be done using only two sets of measurements.

The amount of charge Q that is needed to stimulate the body tissue can be expressed as:

$$Q=I*d.$$

where I is current and d is the pulse duration.

Since the stimulation current can be expressed as:

$$I=I_R*(1+d_c/d)$$

We know that:

$$Q = I_R*(1+d_c/d)*d$$
$$= (I_R*d) + (I_R*d_c)$$
$$= I_R*(d+d_c)$$

If a fixed pulse duration is picked and a stimulation pulse is emitted, e.g., from ventricular pulse generator 80, the ventricular sense amplifier 84, can look for an evoked response. An evoked response will typically occur within a window of 15 to 50 milliseconds. If an evoked response does not occur, the amplitude of the stimulation pulse is increased, e.g., by a relatively small (fine) quantity, and the test is repeated. When an evoked response is detected, a point on the strength-duration curve has been found.

If this test process is repeated twice, one can arithmetically derive the rheobase and the chronaxie. For example, the tests may be repeated at the exemplary values of 1.0 and 2.0 milliseconds (one of ordinary skill in the art can adapt these calculations for other test values. See, for example, Equations 2 and 3 of U.S. Pat. No. 5,447,525 to Powell et al.) and provide the following Q values:

$$Q_2=I_R*(2+d_c)=(2*I_R)+(I_R*d_c)$$

$$Q_1 I_R*(1+d_c)=I_R+(I_R*d_c)$$

Accordingly:

$$Q_2 - Q_1 = I_R$$

i.e., the rheobase current is the difference between the two charges (where Q is in millicoulombs and I is in amperes). If the equation is multiplied by resistance R and the charges are adjusted for their 2.0 millisecond and 1.0 millisecond durations, we determine that:

$$V_R = (2*V_{(2)}) - V_{(1)}$$

i.e., the rheobase voltage can be calculated from the two measured voltages at which capture occurred where $V_{(2)}$ is the measured capture voltage at 2.0 milliseconds and $V_{(1)}$ is the measured capture voltage at 1.0 milliseconds.

Further substituting the solved rheobase value, $(2*V_{(2)}) - V_{(1)}$, in the Lapicque voltage equation at 1.0 milliseconds, we determine that:

$$V = V_R * (1 + d_c/d)$$

$$V_1 = ((2*V_{(2)}) - V_{(1)}) * (1 + d_c/1)$$

$$V_1 = ((2*V_{(2)}) - V_{(1)}) * (1 + d_c)$$

And thus, with measurements made at 1.0 and 2.0 milliseconds:

$$d_c = (V_1/((2*V_{(2)}) - V_{(1)})) - 1$$

In a second alternative technique, the rheobase can be approximated by observing that typically the Lapicque curve is essentially flat at or beyond the 2.0 millisecond point. Thus, if a voltage capture level is obtained at or beyond that point, it will approximate the rheobase. Next, using twice the approximated rheobase value, the pulse duration can be incremented from a starting point, e.g., 0.5 milliseconds, until an evoked response occurs within the detection window. This point of capture may then identified as the chronaxie value. Alternatively, since the measured capture voltage at 2.0 milliseconds is an approximation of the rheobase value, the calculated chronaxie value may be adjusted by a percentage, e.g., 20%, to accommodate the rheobase approximation. In a further alternative, the measured capture voltage (used to approximate the rheobase) can be adjusted by a percentage, e.g., 90%, to more closely approximate the actual rheobase, and this adjusted value may be used to determine the chronaxie value.

In the event that a voltage multiplier (e.g., a doubler or tripler) is needed, it has been disclosed in the aforementioned U.S. Pat. No. 5,697,956 to Bornzin that the use of the voltage multiplier can be postponed if portions of the stimulation energy curve increase the duration component instead of the amplitude component. Accordingly, the aforedescribed stimulation curve 700 of FIG. 8 may be modified to accommodate a voltage multiplier. Accordingly, in the example shown in FIG. 8, the stimulation curve 700 is used, as described above, which transitions to a "pulse duration only" adjustment mode above a predetermined voltage threshold, e.g., 2.5 volts. This threshold being chosen so as to provide a guard band to the voltage multiplier 68 to prevent stimulation pulses that might be voltage limited. One of skill in the art could select any voltage threshold for switching to the pulse duration only mode to optimize current drain, while taking into account any hardware (e.g., the present battery voltage) or software limitations. Furthermore, the stimulation energy curve may be adjusted (as shown in reference to the aforementioned FIG. 7 of U.S. Pat. No. 5,697,956 to Bornzin) to accommodate portions in which amplitude decreases occur in conjunction with pulse duration increases (see points 6 and 14 of Bornzin's FIG. 7 and its associated description).

Accordingly, if a voltage greater than the determined threshold voltage is needed, it may be energy efficient to postpone use of the voltage multiplier 68 and to modify the stimulation energy curve 700 to include a jog 804 where the duration component increases at a fixed voltage, at or below the battery voltage. After the duration component has been allowed to increase by fixed amount or percentage, the amplitude component is then allowed to increase with a corresponding decrease in the duration component by following jog 806. Accordingly, the energy level at point 808 may be selected to be greater than (or optionally identical to) the energy level at point 810. A similar set of jogs, 805 and 807, may be included when a voltage tripler is used. Preferably, the control/timing circuit 86 periodically monitors the battery level using a voltage detector 120 and periodically adjusts the positions of these jogs along the stimulation energy curve 700 accordingly. While this adjustment for a voltage multiplier 68 has been shown in reference to stimulation energy curve 700, a similar adjustment is equally applicable to stimulation energy curve 704 which intersects the quasi-chronaxie point.

Figure 12:
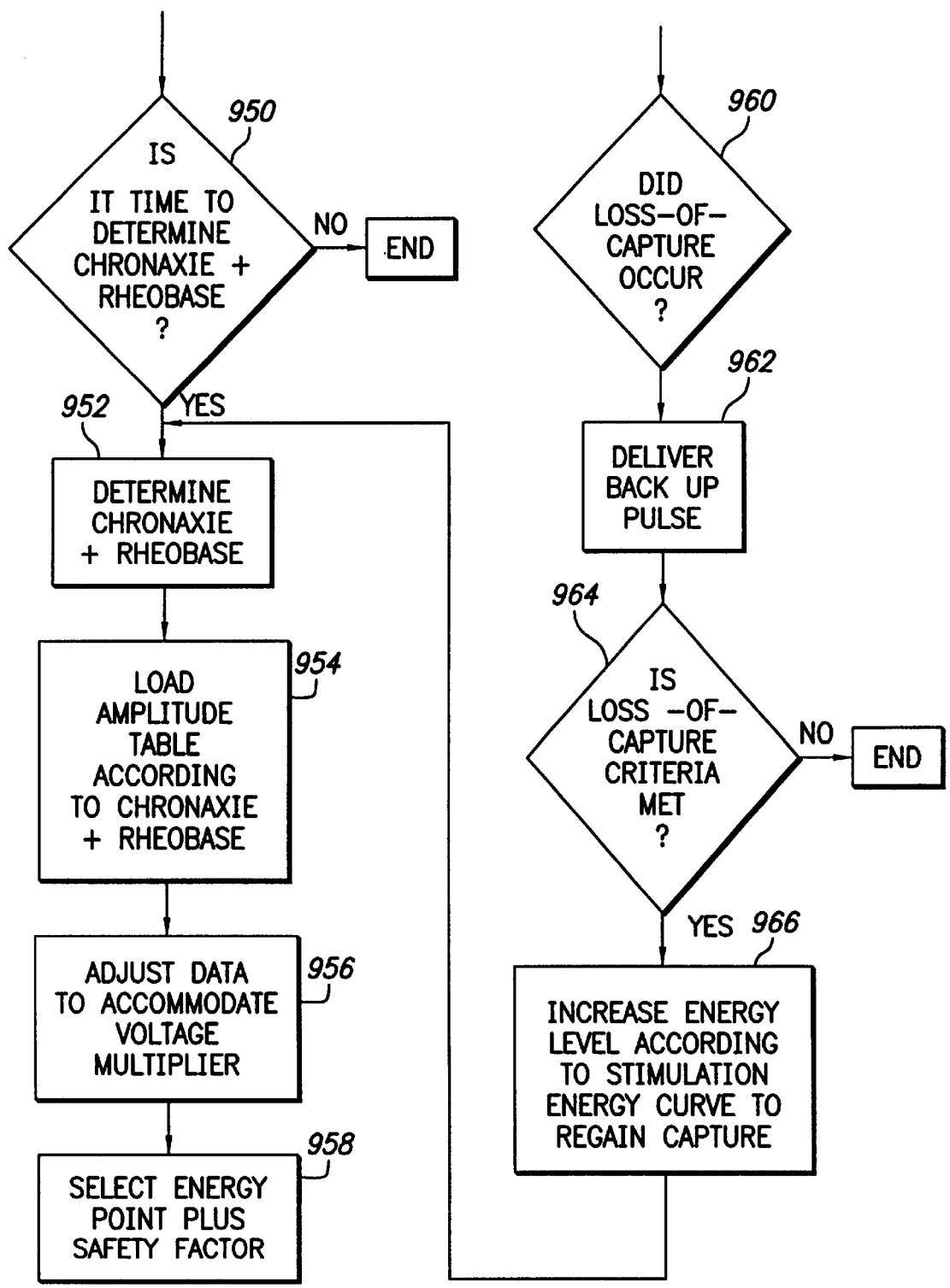
FIG. 12 shows a simplified block diagram of the pertinent features of an exemplary automatic capture/threshold method for use with the preferred stimulation energy curve of the present invention.

FIG. 12 shows a simplified portion of an exemplary automatic capture/threshold method for use with the preferred stimulation energy curve. Periodically, e.g., every six to twenty-four hours, the control/timing circuit 86 determines in step 950 whether it is time to determine the present chronaxie and rheobase values. In step 952, the chronaxie/rheobase determination is made as described above. In step 954, the amplitude/duration table 900 is loaded with pairs of points according to the one of the aforedescribed stimulation energy curves. The pairs of points may be loaded such that they represent fixed increases in energy, fixed increases in voltage (as shown in the exemplary data in the tables of FIGS. 10 and 11) or duration, or percentage increases in energy, i.e., increases in energy that are larger at higher energy levels. Optionally, in step 956, the amplitude/duration table 900 is modified to reflect the present battery voltage and the use of a voltage multiplier. Finally in step 958, an energy point is selected beyond the chronaxie point along the stimulation energy curve (curve 800 in this example) to accommodate a safety margin. This point may be a fixed energy amount greater than the chronaxie point 802, e.g., one or two points further than the chronaxie point in table 900, or a percentage amount determined by the energy level of the current chronaxie point. Additionally, the percentage amount may be programmable from the external programmer 48.

A simplified example of the utility of this concept can be shown in relationship to a fixed duration stimulation energy curve embodiment. For example, in the prior art, a safety margin of 0.3 volts is typically used at the point where capture is achieved. Thus, if capture was achieved at a voltage of 0.6 volts, a subsequent stimulation pulse would use 0.9 volts, i.e., resulting in a safety margin percentage of 50%. However, if capture was achieved at a voltage of 1.0 volts, a subsequent stimulation pulse would use 1.3 volts, i.e., the safety margin percentage would have decreased to 30%. The decrease in safety margin relative to stimulation energy which varies according to the square of the voltage would be even more significant. Accordingly, embodiments of the present invention preferably maintain the safety margin percentage in amplitude or power. For example, if the safety margin is maintained as an amplitude percentage, the 1.0 volt capture level would increase to 1.5 volts.

Following the determination of the chronaxie point 802 plus a safety margin, this point 812 (from the amplitude duration table 900 or calculated as needed by the control/timing circuit 86) is used as the present stimulation pulse when not inhibited by an intrinsic cardiac event. The pacemaker 70, as a parallel task, monitors for the presence of an evoked response to each delivered stimulation pulse. However, should a stimulation pulse at this energy level not capture the cardiac tissue in step 960 (as described further in the User's Manual, ©1998 St. Jude Medical for the Affinity® DR, Model 5330 L/R Dual-Chamber Pulse Generator and in a copending, commonly-assigned application to Paul A. Levine, entitled "An Implantable Cardiac Stimulation Device Having Autocapture/Autothreshold Capability"), a high voltage, e.g., 4.5 volt, backup pulse is generated to ensure capture in step 962. Should a loss-of-capture criteria be met in step 964, e.g., two consecutive losses-of-capture, the stimulation energy level is increased in step 966, preferably by a relatively large (coarse) amount, according to the stimulation energy curve 800. Capture is rapidly regained due to the stimulation energy curve 800 of the present invention, thus minimizing the number of consecutive cardiac cycles requiring backup pulses. Once capture has been regained, the process preferably continues at step 952 where the chronaxie and rheobase are redetermined. This process is also applicable to the use of stimulation energy curve 801 which passes through the quasi-chronaxie point 803.

Finally, a simplified example is described relative to the amplitude/duration data of table 900 in FIG. 10 and the A and B strength-duration curves of FIG. 9. In this example it is assumed that strength-duration curve A was initially determined in step 952 and that the data of table 900 was generated accordingly in step 954. In this example, the data was generated with fixed amplitude increases and correspondingly fixed duration increases accordingly to the aforedescribed stimulation energy equation (see Equation 1):

$$amplitude = duration + 0.35$$

However, fixed duration increases with fixed amplitude increases according to the aforedescribed equation or fixed stimulation energy increases could have also been used. In this case the original chronaxie point 802 was determined to be at an amplitude of 0.70 volts and a duration of 0.30 milliseconds, corresponding to data point 6 (the starting controlled energy level). To accommodate a safety margin, data point 8 (shown as 812 in FIG. 9) is used for the initial stimulation energy level. For purposes of this illustration, we assume that physiological changes have resulted in the cardiac tissue now responding to strength-duration curve B (corresponding to double the chronaxie and double the rheobase from that originally measured for curve A). Accordingly, it is apparent, graphically, that capture will no longer occur. To regain capture, the stimulation energy level is increased along the stimulation energy curve 800 until capture is regained at data point 17 (shown as point 814 in FIG. 9). Due to the quantization amount used, i.e., the step size, data point 16 just misses capture and thus data point 17 must be used. Thus, it may be observed that the efficiency of this implementation is somewhat quantization dependent. Alternatively, if the control/timing circuit 86 performs this calculation as needed without a table, these quantization effects may be limited. Finally, to achieve a safety margin, data point 19 is used as the new stimulation energy level (shown as point 816 in FIG. 9).

In the prior art, only the amplitude of the stimulation voltage would have been changed to regain capture. Accordingly, capture would have been regained at point 818 (2.1 volts, 0.3 milliseconds) and after a safety margin was added, a stimulation energy point 820 (2.4 volts, 0.3 milliseconds) would have been used. Various graphical observations can now be made. First, point 820 is much closer to curve B than point 816. Second, point 816 is much closer to the original chronaxie point 802 than is point 820. Accordingly, capture can be regained faster and with better immunity to measurement variations and variations in chronaxie and rheobase than possible with the prior art. Despite these improvements, the amount of stimulation energy used by points 816 and 820 are essentially identical. If it were not for the aforementioned quantization effects relative to this particular example, there also would have been an energy saving.

Point 816 is only approximately equidistant in amplitude and duration from curve B. This occurs since stimulation energy curve 800 was determined to generate points equidistant in amplitude and duration from the original strength-duration curve, i.e., curve A. Accordingly, steps 952–958 (see FIG. 12) may be processed to determine a new stimulation energy curve 809 and a new stimulation energy point 822 that is optimized for the physiologically altered strength-duration curve B.

Furthermore, a stimulation energy curve that intersects the quasi-chronaxie point 803 may be used, as reflected in FIG. 11. In this particular example, the original operating data point (9) (see FIG. 11) will dissipate a greater amount of power than in the case of FIG. 10. However, the final operating data point (19) (see FIG. 11) will result in a greater energy saving.

Accordingly, what has been shown is an improved stimulation energy curve for performing an automatic capture/threshold procedure in an implantable stimulation device, e.g., for stimulating cardiac or other muscle tissue. While the invention has been described by means of specific embodiments and applications thereof, it is understood that numerous modifications and variations could be made thereto by those skilled in the art without departing from the spirit and scope of the invention. For example, it is believed that the during the acute phase following lead implantation, that shifts in the strength-duration curve predominantly result from rheobase variations. Accordingly during the acute phase, it may be desirable to automatically (or in response to an instruction from the external programmer) disable the stimulation energy curve of the present invention (i.e., a stimulation energy curve in which most portions include concomitant increases in amplitude and duration) and to operate with a unidirectional, e.g., vertical, stimulation energy curve as found in the prior art (e.g., a stimulation energy curve in which the duration component is essentially fixed and only the amplitude component increases). Furthermore, it is recognized that a particular implementation of a stimulation device may have quantization restrictions that limit its ability to implement the preferred linear stimulation energy curve. Thus, an approximation of the preferred linear stimulation energy curve is considered to be within the scope of the present invention. For example, stepwise approximations of a stimulation energy curve, e.g., 809, (see step portion 824 which increases amplitude and then duration and step portion 826 which increases duration and amplitude as shown in FIG. 9) of the preferred linear stimulation energy curve are also considered to be within the scope of the present invention since such approximations (independent of the ratio of the amplitude and duration steps) are considered to be essentially defined by the preferred linear relationship, i.e., $$amplitude = (slope * duration) + offset.$$

Furthermore, any stimulation energy adjustment for regaining capture along the aforementioned stimulation energy curve, independent of the initial starting energy point, is likewise considered to be within the scope of the present invention. It is therefore to be understood that within the scope of the claims, the invention may be practiced otherwise than as specifically described herein.

What is claimed is:

1. An implantable stimulation device configured for stimulating muscle tissue through at least one electrode implanted in electrical contact with selected muscle tissue, the stimulation device comprising:

a pulse generator configured for electrical coupling to the electrode and configured to generate stimulation pulses at a controlled energy level to thereby stimulate the muscle tissue, wherein the controlled energy level is defined by a set of characteristics including an amplitude component and a duration component;

a detection circuit configured for electrical coupling to the electrode and configured to receive signals for determining the presence or absence of an evoked response to each of the stimulation pulses;

a controller, coupled to the pulse generator and the detection circuit, for increasing the controlled energy level from a first energy level to a second energy level in response to a loss-of-capture criteria related to the absence of an evoked response to at least one stimulation pulse generated at the first energy level; and wherein the first energy level has a first amplitude component and a first duration component and the second energy level has a second amplitude component and a second duration component, wherein the second amplitude component exceeds the first amplitude component and the second duration component exceeds the first duration component.

2. The implantable stimulation device of claim 1 wherein the set of characteristics for each energy level is determined by the controller.

3. The implantable stimulation device of claim 1 wherein the set of characteristics for each energy level is predetermined.

4. The implantable stimulation device of claim 1 wherein the set of characteristics for each energy level is remotely programmable.

5. The implantable stimulation device of claim 1 wherein the relationship between the amplitude and duration components is predominantly defined by an essentially linear relationship specified by the equation:

$$\text{amplitude} = (\text{slope} * \text{duration}) + \text{offset}$$

where slope and offset are constant values.

6. The implantable stimulation device of claim 5 wherein the slope is between 0.3 and 3.0 volts/millisecond.

7. The implantable stimulation device of claim 6 wherein the slope is essentially 1.0 volts/millisecond and the offset is a function of a strength-duration curve characterized by a chronaxie and a rheobase.

8. The implantable stimulation device of claim 7 wherein values corresponding to the chronaxie and rheobase are remotely programmable.

9. The implantable stimulation device of claim 7 wherein the controller periodically determines the chronaxie and rheobase.

10. The implantable stimulation device of claim 7 wherein the value of the offset is defined by the equation:

$$\text{offset} = (2 * \text{rheobase}) - \text{chronaxie}$$

where rheobase is in volts and chronaxie is in milliseconds.

11. The implantable stimulation device of claim 7 wherein the offset is defined by the equation:

$$\text{offset} = \text{rheobase}.$$

12. The implantable stimulation device of claim 1 additionally comprising a table for defining a plurality of energy levels defined by amplitude and duration components.

13. The implantable stimulation device of claim 12 wherein the energy levels defined within the table include at least one pair of sequential energy levels where the amplitude component is essentially the same between the sequential energy levels and the duration component increases between the sequential energy levels.

14. The implantable stimulation device of claim 12 wherein the energy levels defined within the table include at least one pair of sequential energy levels where the amplitude component increases between sequential energy levels and the duration component decreases between sequential energy levels.

15. The implantable stimulation device of claim 9 wherein a starting controlled energy level having an amplitude component and a duration component is determined in response to the strength-duration curve and an initial controlled energy level for delivery by the pulse generator is determined by increasing both amplitude and duration components of the starting controlled energy level to achieve a safety margin from the determined strength-duration curve.

16. The implantable stimulation device of claim 15 wherein the initial controlled energy level is greater than the starting controlled energy level by a variable safety margin.

17. A method for stimulating a patient's body tissue, the method comprising the steps of:

periodically delivering a stimulation pulse to the patient's body tissue, the stimulation pulse having a controlled energy level, wherein the controlled energy level is defined by a set of characteristics including an amplitude component and a duration component;

detecting the presence or absence of an evoked response generated by the patient's body tissue in response to the stimulation pulse during a detection window;

determining whether a loss-of-capture criteria is satisfied in response to the absence of an evoked response to at least one stimulation pulse delivered at a first energy level; and concurrently increasing both the amplitude and duration components of the controlled energy level in response to the loss-of-capture criteria until a capture criteria is met.

18. The method of claim 17 additionally comprising the step of periodically determining the set of characteristics for each energy level.

19. The method of claim 17 additionally comprising the step of predetermining the set of characteristics for each energy level.

20. The method of claim 17 additionally comprising the step of remotely programming the set of characteristics for each energy level.

21. The method of claim 17 wherein the step of increasing the amplitude and duration components of the controlled energy level is performed according to an essentially linear relationship specified by the equation:

$$\text{amplitude} = (\text{slope} * \text{duration}) + \text{offset}$$

where slope and offset are constant values.

22. The method of claim 21 additionally comprising the step of setting the slope to a value between 0.3 and 3.0 volts/millisecond.

23. The method of claim 22 additionally comprising the steps of:
setting the slope to a value of essentially 1.0 volts/millisecond; and
setting the offset to a value that is a function of a determined strength-duration curve characterized by a chronaxie and a rheobase.

24. The method of claim 23 additionally comprising the step of setting the offset to a value defined by the equation:

$$offset=(2*rheobase)-chronaxie$$

where rheobase is in volts and chronaxie is in milliseconds.

25. The method of claim 23 additionally comprising the step of setting the offset to a value defined by the equation:

$$offset=rheobase.$$

26. The method of claim 23 additionally comprising the step of periodically determining the chronaxie and rheobase.

27. The method of claim 17 additionally comprising the step of storing within a table a plurality of energy levels defined by amplitude and duration components.

28. The method of claim 27 additionally comprising the step of storing within the table at least one pair of sequential energy levels where the amplitude component is essentially the same between the sequential energy levels and the duration component increases between the sequential energy levels.

29. The method of claim 27 additionally comprising the step of storing within the table include at least one pair of sequential energy levels where the amplitude component increases between sequential energy levels and the duration component decreases between sequential energy levels.

30. The method of claim 23 additionally comprising the steps of:
determining a starting controlled energy level having an amplitude component and a duration component in response to the determined strength-duration curve; and
determining an initial controlled energy level for delivery by the pulse generator by increasing both the amplitude and duration components of the starting controlled energy level to achieve a safety margin from the determined strength-duration curve.

31. The method of claim 30 additionally comprising the step of setting the initial controlled energy level to a value greater than the starting controlled energy level by a variable safety margin.

32. An implantable stimulation device configured for stimulating muscle tissue through at least one electrode implanted in electrical contact with selected muscle tissue, the stimulation device comprising:
a pulse generator configured for electrical coupling to the electrode and configured to generate stimulation pulses at a controlled energy level to thereby stimulate the muscle tissue, wherein the controlled energy level is defined by a set of characteristics including an amplitude component and a duration component;
a detection circuit configured for electrical coupling to the electrode and configured to receive signals for determining the presence or absence of an evoked response to each of the stimulation pulses;
a controller, coupled to the pulse generator and the detection circuit, for increasing the controlled energy level from a first energy level to a second energy level in response to a loss-of-capture criteria related to the absence of an evoked response to at least one stimulation pulse generated at the first energy level; and wherein
the controlled energy level is increased according to a relationship between the amplitude and duration components that is predominantly defined by an essentially linear relationship specified by the equation:

$$amplitude=(slope*duration)+offset$$

where slope and offset are constant values.

33. The implantable stimulation device of claim 32 wherein the set of characteristics for each energy level is determined by the controller.

34. The implantable stimulation device of claim 32 wherein the set of characteristics for each energy level is predetermined.

35. The implantable stimulation device of claim 32 wherein the set of characteristics for each energy level is remotely programmable.

36. The implantable stimulation device of claim 32 wherein the slope is between 0.3 and 3.0 volts/millisecond.

37. The implantable stimulation device of claim 36 wherein the slope is essentially 1.0 volts/millisecond and the offset is a function of a strength-duration curve characterized by a chronaxie and a rheobase.

38. The implantable stimulation device of claim 37 wherein the offset is defined by the equation:

$$offset=(2*rheobase)-chronaxie$$

where rheobase is in volts and chronaxie is in milliseconds.

39. The implantable stimulation device of claim 37 wherein the offset is defined by the equation:

$$offset=rheobase.$$

40. The implantable stimulation device of claim 37 wherein the controller periodically determines the chronaxie and rheobase.

41. The implantable stimulation device of claim 32 additionally comprising a table for defining a plurality of energy levels defined by amplitude and duration components.

42. The implantable stimulation device of claim 41 wherein the energy levels defined within the table include at least one pair of sequential energy levels where the amplitude component is essentially the same between the sequential energy levels and the duration component increases between the sequential energy levels.

43. The implantable stimulation device of claim 41 wherein the sets of energy levels defined within the table include at least one pair of sequential energy levels where the amplitude component increases between sequential energy levels and the duration component decreases between sequential energy levels.

44. The implantable stimulation device of claim 40 wherein a starting controlled energy level having an amplitude component and a duration component is determined in response to the strength-duration curve and an initial controlled energy level for delivery by the pulse generator is determined by increasing both amplitude and duration components of the starting controlled energy level to achieve a safety margin from the determined strength-duration curve.

45. The implantable stimulation device of claim 44 wherein the initial controlled energy level is greater than the starting controlled energy level by a variable safety margin.

46. The implantable stimulation device of claim 44 wherein the starting controlled energy level has an amplitude component of twice the rheobase and a duration component of the chronaxie.

47. The implantable stimulation device of claim 44 wherein the starting controlled energy level corresponds to the intersection between the strength-duration curve and the essentially linear relationship defining the controlled energy level.

48. An implantable stimulation device for stimulating a patient's body tissue, the stimulation device comprising:

means for periodically delivering a stimulation pulse to the patient's body tissue, the stimulation pulse having a controlled energy level, wherein the controlled energy level is defined by a set of characteristics including an amplitude component and a duration component;

means for detecting the presence or absence of an evoked response generated by the patient's body tissue in response to the stimulation pulse; and means for determining whether a loss-of-capture criteria is satisfied in response to the absence of an evoked response to at least one stimulation pulse;

means for increasing the controlled energy level when the loss-of-capture criteria is satisfied according to a relationship between the amplitude and duration components that is predominantly defined by an essentially linear relationship specified by the equation:

$$\text{amplitude} = (\text{slope} * \text{duration}) + \text{offset}$$

where slope and offset are constant values.

49. An implantable cardiac stimulation device comprising:

pulse generator means for providing stimulation pulses to cardiac tissue, such stimulation pulses having selectable pulse shapes, each pulse being defined by a pulse amplitude and pulse width;

detection means for detecting the presence or absence of an evoked response corresponding to each stimulation pulse and indicative thereof of the presence or absence of capture;

control means for controlling the stimulation pulse amplitude and pulse width in response to a loss of capture criteria; and wherein the control means simultaneously increases both the pulse amplitude and pulse width until a capture criteria is met.

50. The stimulation device of claim 49 wherein the pulse amplitude and pulse width are related by the equation:

$$\text{pulse amplitude} = \text{slope} * \text{pulse width} + \text{offset}$$

wherein slope and offset are constant values.

51. The stimulation device of claim 50 wherein the slope is in the range of 0.3 to 3.0 volts/millisecond.

52. The stimulation device of claim 50 wherein the control means includes means for determining the chronaxie and rheobase of the cardiac tissue.

53. The stimulation device of claim 52 wherein the value of the offset is defined by the equation:

$$\text{offset} = (2 * \text{rheobase}) - \text{chronaxie}$$

where rheobase is in volts and chronaxie is in milliseconds.

54. The stimulation device of claim 52 wherein the value of the offset is defined by the equation:

$$\text{offset} = \text{rheobase}.$$

* * * * *